(12) United States Patent
Thorsten et al.

(10) Patent No.: US 8,067,444 B2
(45) Date of Patent: Nov. 29, 2011

(54) PYRIDOXAMINE FOR THE TREATMENT OF DIABETIC INTERMEDIARIES AND POST-AMADORI INHIBITION

(75) Inventors: Degenhardt Thorsten, Durham, NC (US); Schotzinger Robert, Morrisville, NC (US); Fox J. Wesley, Cary, NC (US)

(73) Assignee: NephroGenex, Inc., Research Triangle Park, NC (US)

( * ) Notice: Subject to any disclaimer, the term of this patent is extended or adjusted under 35 U.S.C. 154(b) by 0 days.

(21) Appl. No.: 12/019,819

(22) Filed: Jan. 25, 2008

(65) Prior Publication Data

US 2008/0119525 A1 May 22, 2008

Related U.S. Application Data

(60) Division of application No. 11/513,530, filed on Aug. 31, 2006, now abandoned, which is a continuation of application No. 10/871,224, filed on Jun. 18, 2004, now abandoned.

(60) Provisional application No. 60/480,032, filed on Jun. 20, 2003, provisional application No. 60/562,062, filed on Apr. 14, 2004.

(51) Int. Cl.
  *A61K 31/44* (2006.01)
(52) U.S. Cl. ......... 514/348; 514/277; 514/345; 514/351
(58) Field of Classification Search .................. None
  See application file for complete search history.

(56) References Cited

U.S. PATENT DOCUMENTS

| | | | |
|---|---|---|---|
| 5,254,572 | A | 10/1993 | Serfontein |
| 5,288,716 | A | 2/1994 | Speck |
| 5,985,857 | A | 11/1999 | Hudson et al. |
| 6,228,858 | B1 | 5/2001 | Hudson et al. |
| 6,436,969 | B1 | 8/2002 | Khalifah et al. |
| 6,472,400 | B1 | 10/2002 | Hudson et al. |
| 6,472,411 | B1 | 10/2002 | Hudson et al. |
| 6,489,345 | B1 | 12/2002 | Sethi et al. |
| 6,521,645 | B2 | 2/2003 | Voziyan et al. |
| 6,716,858 | B1 | 4/2004 | Khalifah et al. |
| 6,730,686 | B1 | 5/2004 | Baynes et al. |
| 6,740,668 | B1 | 5/2004 | Baynes et al. |
| 6,750,209 | B1 | 6/2004 | Hudson et al. |
| 6,894,058 | B1 | 5/2005 | Cameron et al. |
| 2002/0128295 | A1 | 9/2002 | Baynes |
| 2003/0013746 | A1 | 1/2003 | Hudson et al. |
| 2003/0181492 | A1 | 9/2003 | Baynes et al. |
| 2004/0220090 | A1 | 11/2004 | Hudson et al. |

FOREIGN PATENT DOCUMENTS

| | | |
|---|---|---|
| CA | 2376029 A1 | 1/2001 |
| WO | 01/13900 A3 | 3/2001 |

OTHER PUBLICATIONS

Jardine et al., Journal of Cardiovascular Pharmacology, 34 (Suppl. 1), S31-34, 1999.*
Rahn et al., Journal of Hypertension, 17(3), 309-317, 1999.*
Wassenberg JJ, Fox JW, Degenhardt TP, Szabo JR, Khalifah RG. Pyridoxamine (Pyridorin™) reduces urinary TGF-b1 in phase 2 clinical studies (PYR-205/207) on type 1 and type 2 diabetic patients with overt nephropathy. J Am Soc Nephrol. 15:729A, 2004.
Bell DH, Degenhardt TP, Szabo JR, Khalifah RG Schotzinger RJ. Investigation of the safety and efficacy of pyridoxamine (Pyridorin™) in patients with diabetic nephropathy (PYR-206). Diabetes 53 Suppl 2:A119, 2004.
McGill JB, Degenhardt TP, Szabo JR, Khalifah RG, Schotzinger RJ. A phase 2 clinical investigation of pyridoxamine (Pyridorin™) in type 1 and type 2 diabetic patients with overt diabetic nephropathy (PYR-205/207). Diabetes 53 Suppl 2:A138, 2004.
Distiller LA, Malik RA, Degenhardt TP, Szabo JR, Khalifah RG, Schotzinger RJ. Clinical investigation of pyridoxamine (Pyridorin™) in type 1 and type 2 diabetic patients with overt diabetic nephropathy (PYR-205/207). Diabetol 47 Suppl 1:A89, 2004.
Cameron NE, Cotter MA, Chen Y, Khalifah R.G. Correction of neurovascular dysfunction in diabetic rats by the novel non-nucleophilic advanced glycation inhibitor BST-4997. Diabetes 53 Suppl 2:A209, 2004.
Khalifah RG, Chen Y, Price D, Booth A. Structure-activity relations of Pyridorin™ and related novel compounds in relation to their mechanism of AGE inhibition. Diabetes 52 Suppl 1:A187, 2003.
Khalifah RG, Chen Y, Price D, Booth A. Structure-activity relations of Pyridorin™ and related novel compounds in relation to their mechanism of AGE inhibition. Diabetol 46 Suppl 2:A406, 2003.
Wassenberg JJ, Knight, ST, Fox JW, Degenhardt TP, Szabo JR, Khalifah RG. The AGE inhibitor pyridoxamine (Pyridorin™) reduces urinary TGF-b1 in diabetic patients with overt nephropathy. J Am Soc Nephrol. 14:395A, 2003.
Degenhardt TP, Khalifah RG, Klaich GM, Schotzinger RJ. Pharmacokinetics, tolerability and biological activity of oral Pyridorin™, a novel AGE inhibitor, in patients with type 1 diabetes and nephropathy. J Am Soc Nephrol 13:652A, 2002.
Khalifah RG, Chen Y, Price DL, Booth AA. Mechanism of action of Pyridorin™ (pyridoxamine), a novel therapeutic for diabetic complications. J Am Soc Nephrol 13:535A, 2002. Khalifah RG, Chen Y, Price DL, Booth AA. Mechanism of inhibition of advanced glycation end products by Pyridorin™, a novel therapeutic for diabetic complications. Diabetol 45 Suppl 2:A393, 2002.
Degenhardt TP, Khalifah RG, Schotzinger RJ. Human pharmacokinetics and metabolism of oral Pyridorin™, a novel therapeutic for diabetic nephropathy. Diabetol 45 Suppl 2:A366, 2002.
Degenhardt TP, Khalifah RG, Schotzinger RJ. Pharmacokinetics of oral Pyridorin™, a novel AGE inhibitor, in human subjects. Diabetes 51 Suppl 2:A185, 2002.
Murphy, P.A., "Alternative Therapies for Nausea and Vomiting of Pregnancy", Obstetrics & Gynecology, Jan. 1998, 91(1):149-155.
Degenhardt, et al. "Pyridoxamine inhibits early renal disease and dyslipidemia in the streptozotocin-diabetic rat", Kidney International, vol. 61, (2002), pp. 939-950.
Michailova, et al., (1992), Clinical Pharmacology Therapy and Toxicology, "Inhibitory effect of vitamin B6 on nonenzymatic glycation of albumin and hemoglobin", pp. 547-548.
Khatami, et al., (1988), Life Sciences, "Inhibitory effects of pyridoxal phosphate, ascorbate and aminoguanidine on nonenzymatic glycosylation", vol. 43, pp. 1725-1731.

* cited by examiner

*Primary Examiner* — Nissa Westerberg
(74) *Attorney, Agent, or Firm* — McDonnell Boehnen Hulbert & Berghoff LLP

(57) ABSTRACT

The present invention provides pharmaceutical compositions comprising dosage units of pyridoxamine, or a pharmaceutically acceptable salt thereof; and a pharmaceutically acceptable carrier, and methods for their use in limiting the progression of renal disease and/or diabetic complications in human diabetic patient.

16 Claims, 11 Drawing Sheets

Figure 1: Summary of Statistical Parameters for Serum Creatinine (PYR-206)

| Patient Subset | Patient Number (N) | Slope (mg/dL/yr) | Change in Slope | P-Value (ANOVA) | P-Value (ProcMix) |
|---|---|---|---|---|---|
| Safety Population | | | | | |
| Placebo | 63 | 0.223 | | | |
| Pyridorin | 65 | 0.178 | -20% | 0.0065 | NS |
| All Patients with a Baseline SCr ≥ 1.3 mg/dL (median value) | | | | | |
| Placebo | 31 | 0.447 | | | |
| Pyridorin | 34 | 0.165 | -63% | <0.0001 | NS |
| Patients with Type 2 Diabetes and a Baseline SCr ≥ 1.3 mg/dL | | | | | |
| Placebo | 19 | 0.519 | | | |
| Pyridorin | 22 | 0.136 | -74% | <0.0001 | NS |
| Patients with Type 2 Diabetes and a Baseline SCr ≥ 1.3 mg/dL being Treated with ACE-I or ARB | | | | | |
| Placebo | 16 | 0.407 | | | |
| Pyridorin | 20 | 0.138 | -66% | 0.0057 | NS |
| Patients with Triglycerides ≥ 158 mg/dL (median value) | | | | | |
| Placebo | 31 | 0.339 | | | |
| Pyridorin | 33 | 0.250 | -26% | 0.0877 | NS |
| Patients with HbA$_{1C}$ ≥ 7.275 % (median value) | | | | | |
| Placebo | 30 | 0.332 | | | |
| Pyridorin | 34 | 0.281 | -15% | 0.0025 | NS |
| Patients with Type 2 Diabetes and a HbA$_{1C}$ ≥ 7.275 % | | | | | |
| Placebo | 16 | 0.409 | | | |
| Pyridorin | 22 | 0.158 | -61% | 0.1338 | NS |

NS: Not significant

Figure 2(a)

Pyridorin™: PYR-206
BASELINE DEMOGRAPHICS

| | Pyridorin™ | | | Placebo | | |
|---|---|---|---|---|---|---|
| | Type 1 Diabetes N=25 | Type 2 Diabetes N=41 | Overall N=66 | Type 1 Diabetes N=25 | Type 2 Diabetes N=42 | Overall N=67 |
| Age (years) | | | | | | |
| Mean ± SD | 39.4 ± 8.7 | 56.0 ± 8.4 | 49.7 ± 11.7 | 41.0 ± 8.9 | 55.7 ± 7.3 | 50.2 ± 10.6 |
| Range | 27 - 55 | 34 - 69 | 27 - 69 | 26 - 58 | 37 - 69 | 26 - 69 |
| Gender (n [%]) | | | | | | |
| Male | 14 (21.2) | 29 (43.9) | 43 (65.2) | 18 (26.9) | 33 (49.3) | 51 (76.1) |
| Female | 11 (16.7) | 12 (18.2) | 23 (34.8) | 7 (10.4) | 9 (13.4) | 16 (23.9) |
| Race (n [%]) | | | | | | |
| Caucasian | 21 (31.8) | 28 (42.4) | 49 (74.2) | 21 (31.3) | 23 (34.3) | 44 (65.7) |
| HbA$_{1c}$ (%) | | | | | | |
| Mean ± SD | 7.58 ± 1.2 | 7.76 ± 1.5 | 7.69 ± 1.4 | 8.07 ± 1.3 | 7.51 ± 1.8 | 7.72 ± 1.6 |
| Range | 6.0 – 10.4 | 4.8 - 10.2 | 4.8 - 10.4 | 6.1 - 11.0 | 5.2 - 12.7 | 5.2 - 12.7 |
| BP (mm Hg) | | | | | | |
| Mean ± SD | 127 ± 14 / 76 ± 7 | 135 ± 15 / 77 ± 9 | 132$^1$ ± 15 / 76 ± 9 | 133 ± 14 / 79 ± 6 | 140 ± 15 / 78 ± 8 | 138 ± 15 / 79 ± 7 |
| Range | 91, 147 / 61, 89 | 106, 167 / 47, 92 | 91, 167 / 47, 92 | 109, 159 / 69, 89 | 119, 174 / 64, 98 | 109, 174 / 64, 98 |

Pyridorin™: PYR-206

BASELINE DEMOGRAPHICS (cont'd)

|  | Pyridorin™ | | | Placebo | | |
|---|---|---|---|---|---|---|
|  | Type 1 Diabetes N=25 | Type 2 Diabetes N=41 | Overall N=66 | Type 1 Diabetes N=25 | Type 2 Diabetes N=42 | Overall N=67 |
| Creatinine (mg/dL) | | | | | | |
| Mean ± SD | 1.26 ± 0.4 | 1.28 ± 0.3 | 1.27 ± 0.3 | 1.38 ± 0.4 | 1.30 ± 0.4 | 1.33 ± 0.4 |
| Range | 0.5 - 2.0 | 0.6 - 2.2 | 0.5 - 2.2 | 0.6 - 2.1 | 0.7 - 2.1 | 0.6 - 2.1 |
| U. Albumin (mg/12 h) | | | | | | |
| Mean ± SD | 812 ± 1285 | 904 ± 954 | 868 ± 1084 | 850 ± 724 | 1173 ± 1456 | 1055 ± 1243 |
| Range | 133 - 6544 | 113 - 4013 | 113 - 6544 | 149 - 3116 | 95 - 6496 | 95 - 6496 |

Figure 3
Pyridorin™; PYR-206
SUMMARY OF ADVERSE EVENTS

| | Pyridorin™ | | | Placebo | | |
|---|---|---|---|---|---|---|
| | Type 1 Diabetes N=25 | Type 2 Diabetes N=40 | Overall N=65 | Type 1 Diabetes N=23 | Type 2 Diabetes N=40 | Overall N=63 |
| Number (%) of Patients: | | | | | | |
| With an AE | 20 (80%) | 39 (98%)[2] | 59 (91%) | 20 (87%) | 33 (83%) | 53 (84%) |
| With Treatment-related AE[1] | 6 (24%)[2] | 11 (28%) | 17 (26%) | 12 (52%) | 9 (23%) | 21 (33%) |
| Who Discontinued Due to AE | 1 (4%) | 3 (8%) | 4 (6%) | 3 (13%) | 3 (8%) | 6 (10%) |
| With an SAE | 1 (4%) | 6 (15%) | 7 (11%) | 1 (4%) | 4 (10%) | 5 (8%) |
| With Treatment-related SAE[1] | 0 (0%) | 0 (0%) | 0 (0%) | 1 (4%) | 0 (0%) | 1 (2%) |
| Who Died | 0 (0%) | 1 (2.5%) | 1 (1.5%) | 0 (0%) | 0 (0%) | 0 (0%) |

[1] Treatment-related was defined as definitely, probably, or possibly related to study drug as determined by the investigator. If a patient experienced more than 1 AE, the patient was counted once at each dose level at which the AE occurred.
[2] $p < 0.05$ Figure 4
PyridorinTM: PYR-206
ADVERSE EVENTS BY BODY SYSTEM

| Number (%) of Patients: | Type 1 Diabetes | | Type 2 Diabetes | | Overall | |
|---|---|---|---|---|---|---|
| | Pyridorin N=25 | Placebo N=23 | Pyridorin N=40 | Placebo N=40 | Pyridorin N=65 | Placebo N=63 |
| Total # of AEs | 112 | 119 | 185 | 217 | 297 | 336 |
| Blood/Lymphatic | 1 (4%) | 0 (0%) | 2 (5%) | 3 (8%) | 3 (5%) | 3 (5%) |
| Cardiac | 1 (4%) | 2 (9%) | 5 (13%) | 2 (5%) | 6 (9%) | 4 (6%) |
| Ear/Labyrinth | - | - | 1 (3%) | 1 (3%) | 1 (2%) | 1 (2%) |
| Endocrine | 2 (8%) | 0 (0%) | 1 (3%) | 0 (0%) | 3 (5%) | 0 (0%) |
| Gastrointestinal | 8 (32%) | 10 (44%) | 19 (48%) | 15 (38%) | 27 (42%) | 25 (40%) |
| General/Administration site condition | 5 (20%) | 6 (26%) | 10 (25%) | 11 (28%) | 15 (23%) | 17 (27%) |
| Infections/Infestations | 12 (48%) | 11 (48%) | 17 (43%) | 19 (48%) | 29 (45%) | 30 (48%) |
| Injury/Poisoning/Compl. | 3 (12%) | 2 (9%) | 5 (13%) | 7 (18%) | 8 (12%) | 9 (14%) |
| Investigations | 4 (16%) | 6 (26%) | 5 (13%) | 9 (23%) | 9 (14%) | 15 (24%) |
| Metabolism/Nutrition | 5 (20%) | 4 (17%) | 7 (18%) | 4 (10%) | 12 (19%) | 8 (13%) |
| Musculoskeletal/Connective Tissue | 8 (32%) | 7 (30%) | 13 (33%) | 14 (35%) | 21 (32%) | 21 (33%) |
| Nervous system | 7 (28%) | 9 (39%) | 10 (25%) | 16 (40%) | 17 (26%) | 25 (40%) |
| Psychiatric | 2 (8%) | 1 (4%) | 0 (0%) | 2 (5%) | 2 (3%) | 3 (5%) |
| Renal/Urinary | 1 (4%) | 2 (8%) | 2 (5%) | 3 (8%) | 3 (5%) | 5 (8%) |
| Reproductive System/Breast | 1 (4%) | 3 (13%) | 1 (3%) | 2 (5%) | 2 (3%) | 5 (8%) |
| Respiratory, Thoracic | 5 (20%) | 2 (9%) | 5 (13%) | 7 (18%) | 10 (15%) | 9 (14%) |
| Skin/Subcutaneous Tissue | 2 (8%) | 3 (13%) | 10 (25%) | 6 (15%) | 12 (19%) | 9 (14%) |
| Vascular | 2 (8%) | 1 (4%) | 7 (18%) | 6 (15%) | 9 (14%) | 7 (11%) |

Figure 5

Pyridorin™: PYR-206
NEUROLOGIC ADVERSE EVENTS SENSORY SYSTEM

| Number (%) of Patients | Pyridorin N=65 | Placebo N=63 |
|---|---|---|
| Areflexia | 2 (3.1%) | 2 (3.2%) |
| Burning Sensation NOS | 0 (0%) | 2 (3.2%) |
| Hyperaesthesia | 1 (1.5%) | 0 (0%) |
| Hypoaesthesia | 2 (3.1%) | 4 (6.3%) |
| Hyporeflexia | 2 (3.1%) | 3 (4.8%) |
| Paraesthesia | 1 (1.5%) | 4 (6.3%) |
| Peripheral Neuropathy NOS | 0 (0%) | 1 (1.6%) |
| Peripheral Neuropathy Aggravated | 0 (0%) | 1 (1.6%) |
| Sensory Loss | 1 (1.5%) | 8 (12.7%) |
| Total[1] | 9 (13.8%) | 25 (39.7%) |

[1] Adverse Events experienced by the same patient more than once for any one category are only counted once, P = 0.001

Figure 6

Pyridorin™: PYR-206

SUMMARY OF TESTS THAT EXCEEDED PREDESIGNATED CUT-OFF

| Number (%) of Patients: | Type 1 Diabetes | | Type 2 Diabetes | | Overall | |
|---|---|---|---|---|---|---|
| | Pyridorin N=25 | Placebo N=23 | Pyridorin N=40 | Placebo N=40 | Pyridorin N=65 | Placebo N=63 |
| ALT > 120 IU/L | 1 (4%) | 1 (4%) | 0 (0%) | 0 (0%) | 1 (2%) | 1 (2%) |
| AST > 88 IU/L | 2 (8%) | 2 (9%) | 0 (0%) | 1 (3%) | 2 (3%) | 3 (5%) |
| Creatinine > 0.5 mg/DL increase from baseline | 3 (12%) | 4 (17%) | 5 (13%) | 10 (25%) | 8 (12%) | 14 (22%) |
| HCT > 5% decrease from baseline | 3 (12%) | 4 (17%) | 6 (15%) | 10 (25%) | 9 (14%) | 14 (22%) |
| WBC < 3000 cells/µL | 1 (4%) | 0 (0%) | 2 (5%) | 1 (3%) | 3 (5%) | 1 (2%) |

Figure 7(a)

PYR-205 / PYR-207
Baseline Demographics

| | Pyridorin<br>N=57 | Placebo<br>N=27 |
|---|---|---|
| Age (years) | | |
| Mean ± SD | 55.5 ± 10.3 | 54.5 ± 8.8 |
| Range | 25-74 | 38-70 |
| Gender (n[%]) | | |
| Male | 47 (82.5%) | 18 (66.7%) |
| Female | 10 (17.5%) | 9 (33.3%) |
| Race (n[%]) | | |
| Caucasian | 45 (78.9%) | 21 (77.8%) |

Figure 7(b)

PYR-205 / PYR-207 Baseline Demographics

| | Pyridorin<br>N=57 | Placebo<br>N=27 |
|---|---|---|
| HbA$_{1C}$ (%) | | |
| Mean ± SD | 7.39 ± 1.61 | 7.50 ± 2.00 |
| Range | 4.30 - 11.90 | 3.60 - 11.40 |
| BP (mmHg) | | |
| Systolic Mean ± SD | 138.6 ± 14.5 | 142.3 ± 14.3 |
| Diastolic Mean ± SD | 77.0 ± 8.6 | 78.2 ± 7.5 |
| Systolic Range | 108.7 - 163.3 | 110.7 - 176.7 |
| Diastolic Range | 52.7 - 96.7 | 64.0 - 92.7 |
| Patients on ACE-I / ARBs | | |
| n (%) | 52 (91%) | 23 (85%) |
| Creatinine (mg/dL) | | |
| Mean ± SD | 1.75 ± 0.64 | 1.91 ± 0.89 |
| Range | 0.71 - 4.23 | 0.75 - 4.33 |
| U. Albumin (mg/12 h) | | |
| Mean ± SD | 957.34 ± 1111.12 | 1224.60 ± 1129.04 |
| Range | 125.95 - 7111.05 | 176.50 - 4590.10 |

Figure 8: Summary of Statistical Parameters for Serum Creatinine (PYR-205/207)

| Patient Subset | Patient Number (N) | Slope (mg/dL/yr) | Percent Change In Slope | P-Value (ANOVA)[1] | P-Value (ProcMix)[1] |
|---|---|---|---|---|---|
| Safety Population | | | | | |
|   Placebo | 27 | 0.745 | | | |
|   Pyridorin | 57 | 0.094 | -87 | 0.0029 | 0.0618 |
| Patients with Type 2 Diabetes | | | | | |
|   Placebo | 22 | 0.867 | | | |
|   Pyridorin | 45 | 0.098 | -89 | 0.0029 | 0.0729 |
| All Patients with a Baseline SCr ≥ 1.3 mg/dL | | | | | |
|   Placebo | 18 | 0.932 | | | |
|   Pyridorin | 42 | 0.098 | -90 | 0.0016 | 0.0446 |
| Patients with Type 2 Diabetes and a Baseline SCr ≥ 1.3 mg/dL | | | | | |
|   Placebo | 14 | 1.094 | | | |
|   Pyridorin | 33 | 0.074 | -93 | 0.0012 | 0.0481 |
| Patients with Type 2 Diabetes and a Baseline SCr ≥ 1.3 mg/dL being Treated with ACE-I or ARB | | | | | |
|   Placebo | 10 | 1.414 | | | |
|   Pyridorin | 25 | 0.035 | -98 | 0.0002 | 0.0106 |

[1] P-value was taken from the treatment by time interaction term for ANOVA and mixed model analyses. At least one post-baseline measurement was required to be included in the ProcMix analysis.

FIGURE 9

COMPARISON OF PYRIDORIN STUDIES TO OTHER DN STUDIES

| Study | Active Group | Control Group | Average F/U | % Decrease in Creatinine Slope | P-value |
|---|---|---|---|---|---|
| RENAAL (Merck) | Losartan (ARB) | Placebo | ~ 3.4 yrs | 13% | 0.0091 |
| IDNT (BMS) | Irbesartan (ARB) | Placebo | ~ 2.6 yrs | 24% | 0.004 |
| PYR-206 | Pyridorin (+ACE-I/ARB) | ACE-I/ARB | 6 months | 20% | 0.0065 |
| PYR-206[1] | Pyridorin (+ACE-I/ARB) | ACE-I/ARB | 6 months | 66% | <0.0001 |
| PYR-205/207 | Pyridorin (+ACE-I/ARB) | ACE-I/ARB | 6 months | 87% | 0.0618[2] |
| PYR-205/207[1] | Pyridorin (+ACE-I/ARB) | ACE-I/ARB | 6 months | 98% | 0.0106[2] |

[1] Sub-group: Type 2 patients on either ACE-I or ARB with baseline serum creatinine of ≥1.3 mg/dL
[2] p-value derived from repeated measure ProcMix analyses

US 8,067,444 B2

PYRIDOXAMINE FOR THE TREATMENT OF DIABETIC INTERMEDIARIES AND POST-AMADORI INHIBITION

CROSS REFERENCE

The present application is a divisional application of U.S. patent application Ser. No. 11/513,530 filed Aug. 31, 2006, now abandoned, which is a continuation of U.S. patent application Ser. No. 10/871,224 filed Jun. 18, 2004, now abandoned, which claims priority to U.S. Provisional Patent Application Ser. Nos. 60/480,032 filed Jun. 20, 2003 and 60/562,062 filed Apr. 14, 2004, each of which is hereby incorporated by reference in its entirety.

BACKGROUND OF THE INVENTION

Nephropathy develops in 30 to 40 percent of patients with Type 1 diabetes, and in an estimated 10 to 15 percent of patients with Type 2 diabetes. An early sign of the disease includes the loss of protein (particularly albumin) into the urine ("proteinuria" or "albuminuria"). As renal damage progresses, patients lose the ability to effectively filter the blood in the glomerulus and can progress to the need for dialysis or transplantation. Diabetic nephropathy, and in particular dialysis and transplantation, is costly both in terms of medical treatment and in lost productivity. Treatment that prevents or limits the development or progression of diabetic nephropathy will meet a significant medical need and provide significant cost savings to the health care system.

Increased levels of advanced glycation end-products (AGEs) in the glomerular basement membrane are regarded as a major contributing factor in the development of diabetic nephropathy. Circulating levels of AGEs are elevated in diabetic patients and increase dramatically when renal function begins to decline. A large body of evidence has demonstrated that pyridoxamine, a potent AGE inhibitor, can dramatically inhibit the progression of kidney disease in treated animals compared to untreated control animals.

SUMMARY OF THE INVENTION

In one aspect, the present invention provides pharmaceutical compositions comprising (a) a dosage unit of 25 mg to 1000 mg of pyridoxamine, or a pharmaceutically acceptable salt thereof; and (b) a pharmaceutically acceptable carrier.

In another aspect, the present invention provides pharmaceutical compositions comprising: (a) pyridoxamine, or a pharmaceutically acceptable salt thereof; and (b) one or more compounds selected from the group consisting of angiotensin converting enzyme inhibitors, angiotensin receptor blockers, beta-blockers, aldose reductase inhibitors, calcium blockers, diuretics, glycosaminoglycans, incretin mimetics, insulin, insulin sensitizers, statins, fibrates, glucose uptake inhibitors, sulfonylureas, superoxide dismutase (SOD) and SOD mimetics, thiamine pyrophosphate and its prodrugs, transketolase inhibitors, other AGE inhibitors that can mechanistically complement post-Amadori-inhibitors, and protein kinase C inhibitors. In a preferred embodiment, the one or more compounds are selected from the group consisting of angiotensin converting enzyme inhibitors and angiotensin receptor blockers, or pharmaceutically acceptable salts thereof.

In a further aspect, the present invention provides methods for limiting the progression of renal disease and/or diabetic complications in a human diabetic patient, comprising administering to the human diabetic patient an amount of pyridoxamine, or a pharmaceutically acceptable salt thereof, effective to limit the progression of renal disease and/or diabetic complications in the diabetic human patient.

BRIEF DESCRIPTION OF THE FIGURES

FIG. 1 is a table summarizing the clinical trial data (PYR-206).

FIG. 2(a)-(b) summarize the baseline patient demographics from the clinical trial (PYR-206).

FIG. 3 summarizes the adverse events from the clinical trial (PYR-206).

FIG. 4 summarizes adverse events by body system (PYR-206).

FIG. 5 summarizes neurological adverse events in the sensory system (PYR-206).

FIG. 6 summarizes tests that exceeded a pre-designated cut-off (PYR-206).

FIG. 7(a)-(b) summarizes the baseline demographics from the second clinical trial (PYR-205/207)

FIG. 8 summarizes the efficacy findings from the second clinical trial (PYR-205/207)

FIG. 9 provides a comparison of the pyridoxamine clinical trial results to the results of clinical trial using other therapeutics to treat diabetic nephropathy.

DETAILED DESCRIPTION OF THE INVENTION

The present invention provides pharmaceutical compositions of pyridoxamine, and methods for using such compositions in human diabetic patients.

In a first aspect, the present invention provides pharmaceutical compositions, comprising (a) 25 to 1000 milligrams of pyridoxamine, or a pharmaceutically acceptable salt thereof; and (b) a pharmaceutically acceptable carrier.

Dosage unit forms of the pharmaceutical compositions of the present invention comprise between 25 mg and 1000 mg of pyridoxamine, or a pharmaceutically acceptable salt thereof. Such dosage unit forms can comprise, for example, 25, 50, 75, 100, 125, 150, 175, 200, 250, 300, 350, 400, 450, 500, 550, 600, 650, 700, 750, 800, 850, 900, 950, or 1000 mg of pyridoxamine, or a pharmaceutically acceptable salt thereof, or any range of such dosage unit forms. In a preferred embodiment, the dosage unit forms of the pharmaceutical compositions comprise between 50 mg and 500 mg of pyridoxamine, or a pharmaceutically acceptable salt thereof. Such dosage unit forms can comprise, for example, 50, 75, 100, 125, 150, 175, 200, 250, 300, 350, 400, 450, or 500 mg of pyridoxamine, or a pharmaceutically acceptable salt thereof. The dosage unit form can be selected to accommodate the desired frequency of administration used to achieve a specified daily dosage of pyridoxamine, or a pharmaceutically acceptable salt thereof, to a patient in need thereof. Preferably the unit dosage form is prepared for once daily or twice daily administration to achieve a daily dosage of between 50 and 2000 mg, more preferably between 100 and 1000 milligrams.

Therapeutic approaches to treating diabetic nephropathy currently follow two strategies: the use of antihypertensive medications to treat hemodynamic factors, and the use of drugs to control blood glucose and the consequences of hyperglycemia (metabolic factors). It has been found that antihypertensive agents can retard the progression of diabetic nephropathy by lowering renal intra-glomerular pressure. Blockade of the renin-angiotensin system is currently the most common approach to achieve this. The angiotensin converting enzyme (ACE) inhibitor, captopril, was first approved for this indication in type 1 diabetes, but it and other ACE inhibitors are routinely also prescribed for nephropathy in type 2 diabetes. Very recently, blockade of the angiotensin 2 (type 1) receptor (ARB) has been demonstrated to have value, with losartan and irbesartan getting FDA approval for the treatment of nephropathy due to type 2 diabetes mellitus. Other modalities include use of diuretics (thiazides), beta blockers and calcium blockers. However, it is recognized that these treatments generally retard but do not prevent the progression of diabetic renal disease beyond their anti-hypertensive actions.

The second approach to treatment is to treat metabolic factors associated with elevated glucose (hyperglycemia). Strict glucose control is attempted with insulin, insulin sensitizers, insulin secretalogues, metformin, inhibitors of glucose absorption from the gastrointestinal tract and similar medications. However, perfect glucose control cannot be achieved, and it is recognized that even diabetics maintaining excellent glucose control will still experience damaging fluctuations of their glucose in the blood. Other medications are being developed to halt damage from hyperglycemia, such as protein kinase C inhibitors, superoxide dismutase (SOD) and SOD mimetics, thiamine pyrophosphate and its prodrugs, transketolase inhibitors, other AGE inhibitors that can mechanistically complement post-Amadori-inhibitors, glucosaminoglycans, and aldose reductase inhibitors.

A newer approach that can be combined with all the metabolic and hemodynamic therapies is to use agents that halt the direct damage that glucose causes to proteins. Pyridoxamine represents the most promising of this class of compounds designed as inhibitors of the formation of toxic advanced glycation end products that contribute to diabetic complications. Pyridoxamine can be used with these other medications to optimize treatments of general patient populations or with specific patient subpopulations that resist treatment by these other modalities. For example, it is recognized that not all patients tolerate ACE inhibitors or respond to them, but it is possible that the combination with pyridoxamine may prove to be superior to these therapies. Such co-administration of current therapeutics with pyridoxamine may also permit administration of lower dosages of these other therapeutics, thus minimizing potential side effects.

Thus, in a further aspect, the present invention provides pharmaceutical compositions comprising (a) pyridoxamine, or a pharmaceutically acceptable salt thereof; and (b) one or more compounds that can provide hemodynamic and/or metabolic improvement in a human patient, or pharmaceutically acceptable salts thereof. In a preferred embodiment, such compounds are selected from the group consisting of angiotensin converting enzyme inhibitors (ACE-I), angiotensin receptor blockers (ARB), beta-blockers, aldose reductase inhibitors, calcium blockers, diuretics, glycosaminoglycans, incretin mimetics, insulin, insulin sensitizers, statins, fibrates, glucose uptake inhibitors, sulfonylureas, superoxide dismutase (SOD) and SOD mimetics, thiamine pyrophosphate and its prodrugs, transketolase inhibitors, other AGE inhibitors that can mechanistically complement post-Amadori-inhibitors, and protein kinase C inhibitors. The combination of such compounds with pyridoxamine is demonstrated herein to be effective for limiting the progression of renal disease and diabetic complications in human diabetic patients.

In a preferred embodiment of this aspect of the invention, the one or more compounds are selected from the group consisting of angiotensin converting enzyme inhibitors and angiotensin receptor blockers, or pharmaceutically acceptable salts thereof, in a pharmaceutically acceptable carrier. Non-limiting examples of angiotensin converting enzyme inhibitors for use in the present invention include benazepril, benazeprilat, captopril, delapril, fentiapril, fosinopril, libenzapril, moexipril, pentopril, perindopril, pivopril, quinapril, quinaprilat, ramipril, spirapril, spiraprilat, zofenopril, ceronapril, enalapril, indolapril, lisinopril, alacepril, and cilazapril, or pharmaceutically acceptable salts thereof.

Non-limiting examples of angiotensin receptor blockers for use in the present invention include losartan, candesartan, irbesartan, olmesartan, valsartan, telmisartan, eprosartan, and tasosartan.

Pharmaceutically acceptable salts in accordance with the present invention, are salts with physiologically acceptable bases and/or acids well known to those skilled in the art of pharmaceutical technique. Suitable salts with physiologically acceptable bases include, for example, alkali metal and alkaline earth metal salts, such as sodium, potassium, calcium and magnesium salts, and ammonium salts and salts with suitable organic bases, such as methylamine, dimethylamine, trimethylamine, piperidine, morpholine and triethanolamine. Suitable salts with physiologically acceptable acids include, for example, salts with inorganic acids such as hydrohalides (especially hydrochlorides or hydrobromides), sulphates and phosphates, and salts with organic acids.

The pharmaceutical compositions of this aspect of the invention include admixtures of the pyridoxamine, or pharmaceutically acceptable salt thereof, and the one or more other compounds, as well as separate unit dosages of each that are manufactured for combinatorial use. Such separate unit dosages may be administered concurrently or sequentially as determined by the clinician.

In all aspects of the pharmaceutical compositions of the present invention, the compounds are combined with one or more pharmaceutically acceptable carriers appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In a preferred embodiment of each of the above aspects of the invention, the pharmaceutical compositions of the invention are prepared for oral administration. As such, the pharmaceutical composition can be in the form of, for example, a tablet, a hard or soft capsule, a lozenge, a cachet, a dispensable powder, granules, a suspension, an elixir, a liquid, or any other form reasonably adapted for oral administration. The pharmaceutical compositions can further comprise, for example, buffering agents. Tablets, pills and the like additionally can be prepared with enteric coatings. Unit dosage tablets or capsules are preferred.

Pharmaceutical compositions suitable for buccal administration include, for example, lozenges comprising pyridoxamine, or a pharmaceutically acceptable salt thereof and a flavored base, such as sucrose, acacia tragacanth, gelatin, and/or glycerin.

Liquid dosage forms for oral administration can comprise pharmaceutically acceptable emulsions, solutions, suspensions, syrups, and elixirs containing inert diluents commonly used in the art, such as water. Such compositions can also comprise, for example, wetting agents, emulsifying and suspending agents, and sweetening, flavoring, and perfuming agents.

These pharmaceutical compositions can be prepared by any suitable method that includes the step of bringing into association pyridoxamine, or a pharmaceutically acceptable salt thereof (and optionally the other compounds) and the pharmaceutically acceptable carrier. In general, the compositions are prepared by uniformly and intimately admixing the pyridoxamine, or a pharmaceutically acceptable salt thereof, with a liquid or finely divided solid carrier, or both, and then, if necessary, shaping the product. For example, preparation of tablets can comprise compressing or molding a powder or granule of the compound. Compressed tablets can be prepared by compressing, in a suitable machine, the compound in a free-flowing form, such as a powder or granules optionally mixed with a binding agent, lubricant, inert diluent and/or surface active/dispersing agent(s). Molded tablets can be made by molding, in a suitable machine, the powdered compound moistened with an inert liquid diluent.

In another aspect, the present invention provides methods for limiting the progression of renal disease and/or diabetic complications in a diabetic human patient by administering to the patient an amount of pyridoxamine, or a pharmaceutically acceptable salt thereof, effective to limit the progression of renal disease or diabetic complications in the diabetic patient. In a preferred embodiment, the methods comprise administering the pharmaceutical compositions of the invention to the patient. Thus, a preferred embodiment of the method comprises administering between 50 and 2000 milligrams of pyridoxamine, or a pharmaceutically acceptable salt thereof, to the patient, more preferably between 100 and 1000 milligrams of pyridoxamine, or a pharmaceutically acceptable salt thereof.

As used herein, "diabetic patient" encompasses both Type 1 and Type 2 diabetic patients and "diabetes" encompasses both Type 1 and Type 2 diabetes.

As used herein, "limiting the progression of renal disease" means to reduce or prevent decreases in renal function in those patients receiving treatment relative to diabetic patients not receiving the treatment. Such treatment thus reduces the need for kidney dialysis or transplantation in diabetic patients.

The progression of renal disease can be measured in various ways, including the following:

(a) Proteinuria (ie: increased loss of protein into the urine; often assessed by measurement of albumin levels (ie: "albuminuria"));

(b) Impaired glomerular filtration (ie: kidney function to clear substances from blood; can be measured, for example, by creatinine (ie: "impaired creatinine clearance"), inulin, or urea clearance);

(c) Increased levels of serum creatinine; and (d) Increased levels of urinary transforming growth factor beta (TGF-$\beta$).

Thus, the methods of the invention can be used, for example, to limit the increase in one or more of proteinuria, albuminuria, serum creatinine levels, and urinary TGF-$\beta$ levels, and/or to limit the impairment of glomerular filtration and/or creatinine clearance in a diabetic patient being treated with pyridoxamine, a pharmaceutically acceptable salt thereof, or one of the pharmaceutical compositions of the invention relative to a diabetic patient not receiving such treatment. As will be understood by those of skill in the art, a favorable effect of the methods of the invention on any one or more of these measures of renal disease constitutes limiting the progression of renal disease.

In a preferred embodiment, measuring urinary TGF-$\beta$ comprises concentrating urinary samples according to standard protocols (for example, use of an Ultra-4 concentrator), and measuring the urinary concentration at a desired time point after initiation of treatment.

As used herein, "limiting the progression" of diabetic complications means slowing or stopping the progression of diabetic complications in those patients receiving treatment relative to diabetic patients not receiving the treatment. Thus, the methods of the invention can be used, for example, to slow or stop the progression of nephropathy, neuropathy, retinopathy, and/or symptoms due to impaired microvascular (e.g. erectile dysfunction, angina, claudication) or macrovasular (MI, CVA, amputation, etc.) complications of diabetes in diabetic patients receiving treatment relative to diabetic patients not receiving such treatment.

As used herein, "nephropathy" refers to kidney disease, inflammation, or damage; "neuropathy" refers to a disease, inflammation, or damage to the nervous system; symptoms include numbness, tingling, pain, or muscle weakness, depending on the nerves affected. In a further preferred embodiment, the methods serve to limit one or more symptoms of neuropathy selected from the group consisting of areflexia (reflexes absent), hyporeflexia (weakened reflexes), paresthesia (abnormal sensation, such as burning, pricking, or numbness), peripheral neuropathy (disease, inflammation, or damage to the peripheral nervous system), aggravated peripheral neuropathy, and sensory loss (partial or complete loss of sensory function). As used herein, "retinopathy" refers to a disease, inflammation, or damage to the retina.

In a preferred embodiment of this aspect of the invention, the human diabetic patient has type II diabetes.

In further preferred embodiment of the methods of the invention described above, the human diabetic patient being treated has a baseline serum creatinine concentration of greater than or equal to 1.3 mg/dL.

In a further embodiment of the methods of the invention, the methods further comprise administering the pyridoxamine, or a pharmaceutically acceptable salt thereof, in combination with a further therapeutic to limit the progression of renal disease in a human diabetic patient. Such therapeutics include, but are not limited to, angiotensin converting enzyme inhibitors (ACE-I), angiotensin receptor blockers (ARB), beta-blockers, aldose reductase inhibitors, calcium blockers, diuretics, glycosaminoglycans, incretin mimetics, insulin, insulin sensitizers, statins, fibrates, glucose uptake inhibitors, sulfonylureas, superoxide dismutase (SOD) and SOD mimetics, thiamine pyrophosphate and its prodrugs, transketolase inhibitors, other AGE inhibitors that can mechanistically complement post-Amadori-inhibitors, and protein kinase C inhibitors. The further therapeutic can be administered together as a single formulation with or separately from the pyridoxamine, or a pharmaceutically acceptable salt thereof. In a preferred embodiment, the one or more further therapeutics comprise ACE-I and/or ARBs. In a further preferred embodiment, the human diabetic patient is one that has failed to adequately respond to treatment with ACE-I and/or ARBs. As used herein, "failed to respond adequately" means that one or more measures of the progression of renal disease (proteinuria, albuminuria, serum creatinine levels, impaired glomerular filtration, impaired creatinine clearance) continue to increase despite treatment with the ACE-I and/or ARBs.

In a farther preferred embodiment of the various methods of the invention, the human diabetic patient has elevated blood lipid levels, including hyperlipidemia, hypertriglyceridemia, and/or hypercholesterolemia. Such patients tend to have accelerated progression of renal disease relative to other diabetic patients, and the data presented herein demonstrate that treatment of these patients with pyridoxamine is more effective than treatment with the current standard of care for diabetic kidney disease.

The data presented herein also demonstrate that patients with poor glycemic control receive additional benefit from the methods of the invention. Thus, in a further embodiment of the various methods described above, the human diabetic patient is one with poor glycemic control. As used herein, "poor glycemic control" means that the patient has an abnormal glycated hemoglobin level. The most widely accepted measure of glycemic control is the whole blood level of hemoglobin A1C (HbA1C) (a glycosylated hemoglobin), with $\leqq 6.5\%$ HbA1C considered normal. In a preferred embodiment, the patient has a whole blood HbA1C level of greater than 6.5%; in further preferred embodiments, the patient has a whole blood HbA1C level of greater than 6.75%, 7%, 7.25%, or 7.275%.

While not being bound by any specific mechanism of action, it is believed that the beneficial effects of the methods of the invention may be due to the inhibitory effect of pyridoxamine on the formation of advanced glycation end products (AGEs).

The experiments detailed below provide a striking demonstration of the efficacy of pyridoxamine dihydrochloride on limiting renal disease progression in human diabetic patients compared to patients treated with a placebo. It should be noted that the placebo included the current standard of care for human diabetic patients: Antihypertensive care including the use of ACE-I or ARB treatment and treatment of hyperglycemia and hyperlipidemia, while pyridoxamine dihydrochloride was co-administered with ACE-I and/or ARB. Therefore, the beneficial effect of pyridoxamine dihydrochloride is in addition to any benefit the patient would receive via administration of the current standard of care.

Example

A randomized, double-blind, placebo-controlled, multi-center trial which examined the safety profile of pyridoxamine dihydrochloride (PYR) in patients with type 1 and type 2 diabetes mellitus ("DM") and overt nephropathy was conducted ("206 study"). 128 patients (48 type 1, 80 type 2) at 32 sites were randomized to receive either PYR 50 mg twice a day (b.i.d) or placebo for six months. 58 patients in each group completed the study. Groups were well matched at baseline for age, race, gender, blood pressure, hemoglobin A1C (HbA1C), and angiotensin converting enzyme inhibitor (ACEI)/angiotensin receptor blocker (ARB) use.

Baseline characteristics of the patients included serum creatinine=1.27 mg/dL and urinary albumin excretion=868 mg/12 h in treatment, versus 1.33 mg/dL and 1055 mg/12 h in placebo groups (differences not significant, NS).

No significant differences in treatment-related adverse events (26% PYR, 33% placebo), study discontinuation due to AE's (6% PYR, 10% placebo), serious adverse events (11% PYR, 8% placebo), or scored neurotoxicity testing occurred during the study.

The mean rate of rise in serum creatinine was 0.223 mg/dL/yr in placebo and 0.178 mg/dL/yr in treatment groups (p=0.0065 by ANOVA).

In patients with baseline serum creatinine $\geqq 1.3$ mg/dL (baseline median value), the rate was 0.45 mg/dL/yr in placebo and 0.17 mg/dL/yr in PYR groups (p<0.0001, ANOVA).

In addition, type 2 diabetic patients with a baseline serum creatinine of $\geqq 1.3$ mg/dL, the mean rate of rise in serum creatinine was 0.519 and 0.136 (p<0.0001, ANOVA) in placebo and PYR groups, respectively. In a third population of type 2 diabetic patients taking either an ACE-I or ARB with a baseline serum creatinine $\geqq 1.3$ mg/dL, the rate of rise in serum creatinine was 0.138 mg/dL/yr in the PYR group and 0.407 mg/dL/yr in the placebo group (p<0.0057, ANOVA) (See Table 8). PYR substantially reduced the rate of increase in serum creatinine by approximately 60-70%. A treatment effect of PYR to reduce the rate of urinary albumin excretion was observed and was statistically significant using an ANOVA analysis. However, when another method of analysis using repeated measure procedures, as the ones used for the PYR-205/207 study (see below), was applied the treatment differences were no longer statistically significant. Clinical studies with Pimagedine, another agent inhibiting AGE formation, indicate that urinary albumin excretion was not substantially reduced until at approximately one year after initiation of treatment with this inhibitor of AGE formation. Thus, a temporal dissociation exists between changes in serum creatinine and urinary albumin excretion with treatment using AGE inhibitors. This temporal dissociation explains the inability to see a significant reduction in albumin excretion during the 6 month PYR-206 study. Most importantly, the changes in serum creatinine, which is considered a validated marker of renal function, are meaningful and consistent with the observations in the higher dose study PYR-205/207.

A summary of data in the 206 study is shown in FIG. 1. FIG. 2 provides baseline demographics for the study patient population. FIGS. 3 and 4 summarize adverse event data, while FIG. 5 demonstrates that treatment with PYR also significantly reduced the incidence of sensory system neurologic adverse events.

FIG. 6 provides a summary of tests that exceeded predesignated a cut-off.

FIG. 7 provides a comparison of the results of the pyridoxamine clinical trial to previous clinical trials evaluating ACE-I and ARBs.

In addition, the urinary levels of TGF beta in the subjects completing the PYR206 study (combined type 1 and type 2 patients) were tested. This growth factor is an important and accepted marker of renal disease, since it initiates or controls a cascade of cellular changes (from diabetes and other diseases) that lead to mesangial expansion and eventually fibrosis in the kidney. An analysis of the data indicates that while the levels of TGF beta (normalized to urinary creatinine values and thus expressed as a ratio of pg TGF/mg Cr) increased 43% in the placebo subjects during the six month duration of the study, the corresponding values decreased about 24% in the PYR treated group (data not shown). This is strong evidence of the action of PYR in retarding or halting the nephropathy due to the diabetes.

In a separate study ("205/207 study"), diabetic nephropathy patients received six months of treatment of escalating doses of pyridoxamine dihydrochloride (50 mg, 100 mg, and 250 mg), administered orally via capsules twice daily as follows:

50 mg bid for 2 weeks, then if tolerated:
100 mg bid for 2 weeks, then if tolerated:
250 mg bid for 20 weeks.

The study drug was administered in addition to standard of care therapy. The patient population consisted of male and female patients between 18 and 70 years of age with diabetic nephropathy associated with type 1 or type 2 diabetes, serum creatinine of ≦3.5 mg/dL, and macroalbuminuria confirmed with baseline urinary albumin excretion ≧300 mg/24 hrs.

84 patients received at least one dose of the study drug (57 PYR; 27 placebo).

Baseline characteristics of the patients included serum creatinine of 1.75 mg/dL and urinary albumin excretion of 957 mg/12 h in treatment, versus 1.91 mg/dL and 1225 mg/12 h in placebo groups (FIG. 7b).

No significant differences in treatment-related adverse events (35.1% PYR, 44.4% placebo) or study discontinuation due to AE's (8.8% PYR, 7.4% placebo) were observed. There was a higher rate of serious adverse events in patients receiving pyridoxamine 21.1% PYR, 3.7% placebo. Based on a review of similar studies, this imbalance is believed to be the result of an unexpectedly low rate of serious adverse events in the placebo group. None of the treatment-related serious adverse events were considered by independent medical reviewers to be related to pyridoxamine dihydrochloride treatment.

In this higher dose study with pre-specified populations for statistical analyses, benefits of the study drug on various surrogate markers of diabetic renal disease were similar to those disclosed above for the first study (PYR-206). The mean rate of rise in serum creatinine was 0.745 mg/dL/yr in placebo and 0.094 mg/dL/yr in PYR groups (p=0.0618 by ProcMix repeated measure analysis). In addition, in type 2 diabetic patients with a baseline serum creatinine of ≧1.3 mg/dL, the mean rate of rise in serum creatinine was 1.094 and 0.074 (p=0.0481 by ProxMix repeated measure analysis) in placebo and PYR groups, respectively. In a third population of type 2 diabetic patients taking either an ACE-I or ARB with a baseline serum creatinine ≧1.3 mg/dL, the rate of rise in serum creatinine was 0.035 mg/dL/yr in the PYR group and 1.414 mg/dL/yr in the placebo group (p=0.0106, by ProcMix repeated measure analysis) (See Table 9). Urinary TGF-β1 levels increased by 55.7% in the placebo group while mean levels decreased by 13.1% in the PYR group. Due to the small number of adverse events in the sensory system, the same analysis as reported in PYR-206 would not have yielded meaningful results.

A summary of data in the 205/207 study is shown in FIG. 8. FIG. 9 provides a comparison of the results of the pyridoxamine clinical trial to previous clinical trials evaluating ACE-I and ARBs.

We claim:

1. A method for treating diabetic nephropathy in a human diabetic patient comprising orally administering to a human diabetic patient with a baseline serum creatinine concentration of greater than or equal to 1.3 mg/dL between 100 mg and 600 mg per day of pyridoxamine, or a pharmaceutically acceptable salt thereof, wherein the human diabetic patient has diabetic nephropathy, macroalbuminuria, and type II diabetes, and wherein the human diabetic patient is being treated with angiotensin converting enzyme inhibitor therapy or angiotensin receptor blocker therapy.

2. The method of claim 1, wherein the human diabetic patient has failed to respond adequately to angiotensin converting enzyme inhibitor therapy or angiotensin receptor blocker therapy.

3. The method of claim 1, wherein the pyridoxamine, or a pharmaceutically acceptable salt thereof, is administered once or twice a day.

4. The method of claim 2, wherein the pyridoxamine, or a pharmaceutically acceptable salt thereof, is administered once or twice a day.

5. The method of claim 1, wherein the pyridoxamine, or a pharmaceutically acceptable salt thereof, is administered as an oral dosage form selected from the group consisting of a 50 mg oral dosage form, a 75 mg oral dosage form, a 100 mg oral dosage form, a 125 mg oral dosage form, a 150 mg oral dosage form, a 175 mg oral dosage form, a 200 mg oral dosage form, a 250 mg oral dosage form, and a 300 mg oral dosage form.

6. The method of claim 5, wherein the oral dosage form is administered once or twice a day.

7. The method of claim 5, wherein the oral dosage form is selected from the group consisting of a 50 mg oral dosage form, a 250 mg oral dosage form, and a 300 mg oral dosage form.

8. The method of claim 7, wherein the oral dosage form is administered once or twice a day.

9. The method of claim 2, wherein the pyridoxamine, or a pharmaceutically acceptable salt thereof, is administered as an oral dosage form selected from the group consisting of a 50 mg oral dosage form, a 75 mg oral dosage form, a 100 mg oral dosage form, a 125 mg oral dosage form, a 150 mg oral dosage form, a 175 mg oral dosage form, a 200 mg oral dosage form, a 250 mg oral dosage form, and a 300 mg oral dosage form.

10. The method of claim 9, wherein the oral dosage form is administered once or twice a day.

11. The method of claim 9, wherein the oral dosage form is selected from the group consisting of a 50 mg oral dosage form, a 250 mg oral dosage form, and a 300 mg oral dosage form.

12. The method of claim 11, wherein the oral dosage form is administered once or twice a day.

13. The method of claim 1, wherein between 100 mg and 600 mg per day of pyridoxamine, or a pharmaceutically acceptable salt thereof is administered to the human diabetic patient.

14. The method of claim 13, wherein the pyridoxamine, or a pharmaceutically acceptable salt thereof, is administered once or twice a day.

15. The method of claim 13, wherein the pyridoxamine, or a pharmaceutically acceptable salt thereof, is administered as an oral dosage form selected from the group consisting of a 50 mg oral dosage form, a 250 mg oral dosage form, and a 300 mg oral dosage form.

16. The method of claim 15, wherein the oral dosage form is administered once or twice a day.

* * * * *